United States Patent [19]

Wedeen

[11] Patent Number: 4,606,335
[45] Date of Patent: Aug. 19, 1986

[54] CERCLAGE WIRE PASSER

[75] Inventor: Robert S. Wedeen, Coatesville, Pa.

[73] Assignee: Highland Orthopedic Center, Cochranville, Pa.

[21] Appl. No.: 642,366

[22] Filed: Aug. 20, 1984

[51] Int. Cl.[4] ............................................. A61F 5/04
[52] U.S. Cl. .............................. 128/92 E; 128/92 R; 128/303 R
[58] Field of Search .............. 128/92 E, 92 R, 303 R, 128/20

[56] References Cited

U.S. PATENT DOCUMENTS

| | | |
|---|---|---|
| 2,695,607 | 11/1954 | Hipps . |
| 2,897,820 | 8/1959 | Tauber . |
| 3,835,849 | 9/1974 | McGuire . |
| 3,955,568 | 5/1976 | Neufeld . |
| 4,263,904 | 4/1981 | Judet . |
| 4,312,337 | 1/1982 | Donohue . |
| 4,509,516 | 4/1985 | Richmond ...................... 128/303 R |

OTHER PUBLICATIONS

Zimmer, Warsaw, IN, Catalog 1978, p. B5, Beath Pin.
Down Bros. and Mayer & Phelps, Ltd., Toronto, Canada & London, England, Orthopaedic Catalog, p. G67, 20th edition.
Howmedica, Inc. (C) 1978—D-104 Instrumentation Cerclage Instruments.

*Primary Examiner*—Gene Mancene
*Assistant Examiner*—C. W. Shedd
*Attorney, Agent, or Firm*—Connolly and Hutz

[57] ABSTRACT

A cerclage wire passer comprises a proximal portion with handle structure and an S-shaped distal portion with an eyelet hole at the outer end thereof. The S-shaped distal portion includes a primary curved segment that fits around the bone to be cerclaged and a secondary reverse curved segment which accommodates the mass of tissue and muscle surrounding the bone when the wire passer is manipulated.

12 Claims, 9 Drawing Figures

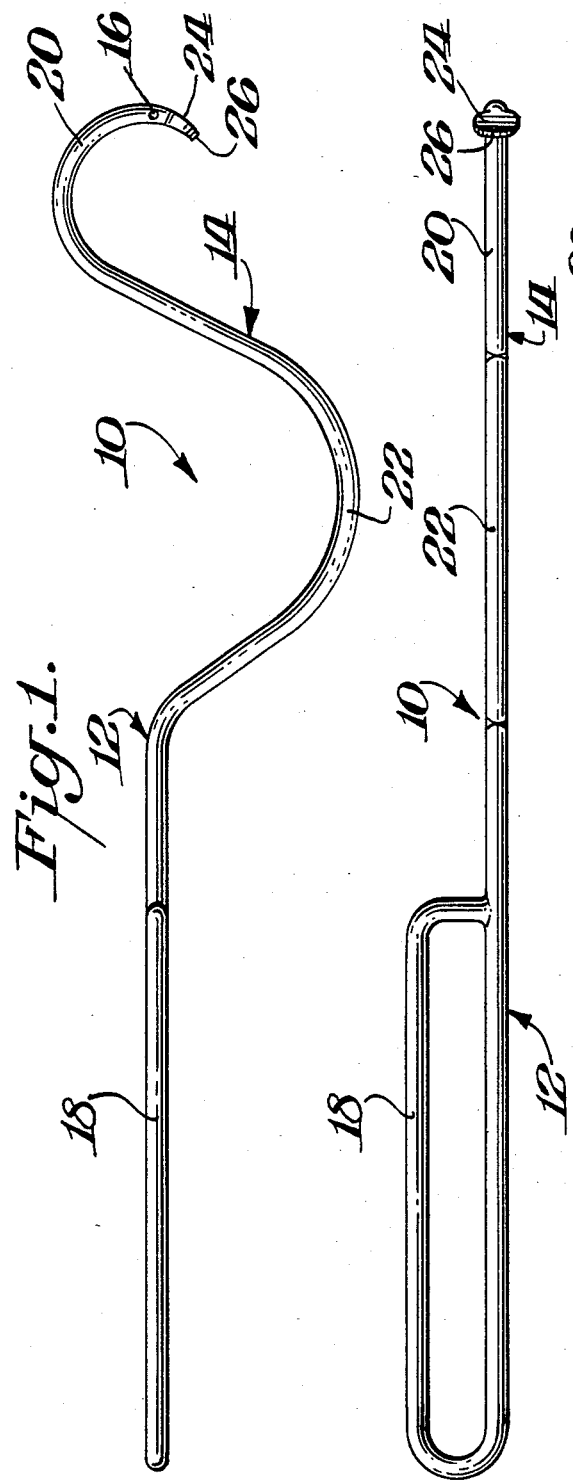
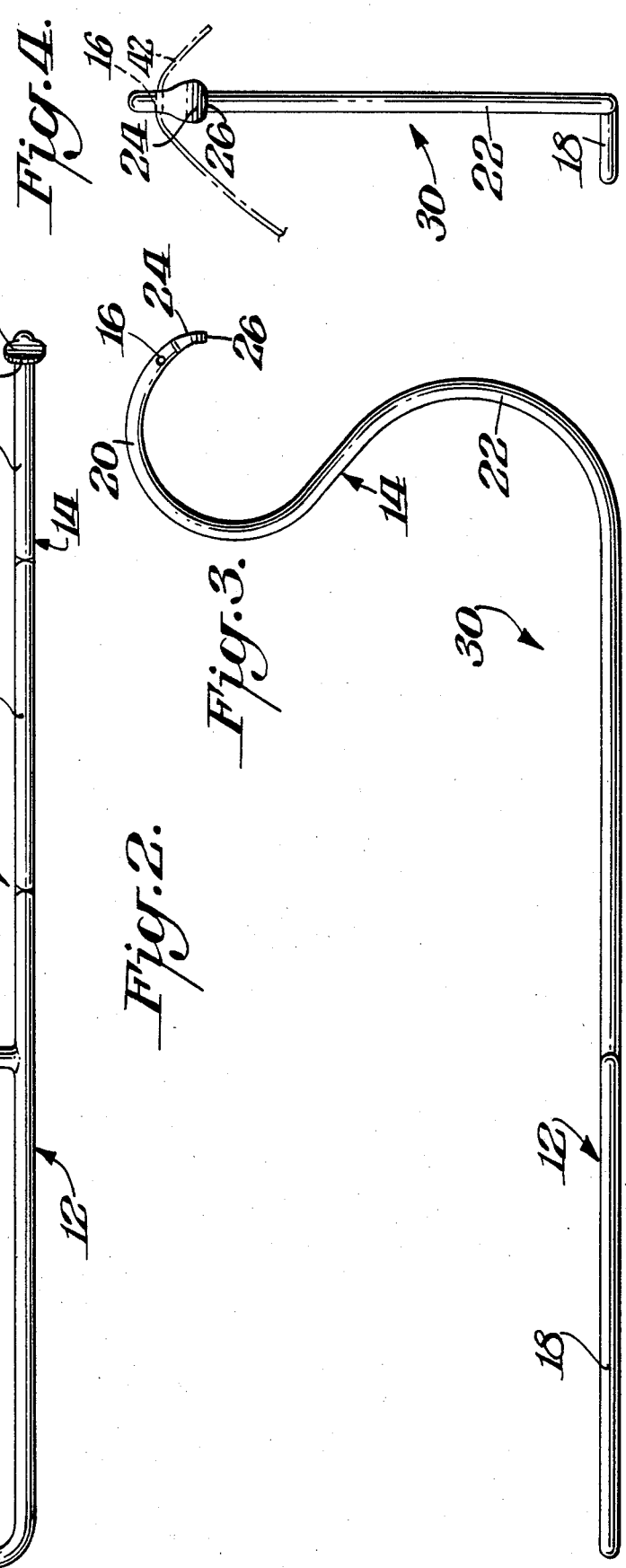

CERCLAGE WIRE PASSER

BACKGROUND OF THE INVENTION

The present invention relates to a cerclage wire passer, and more particularly to an instrument used to position orthopedic wire around a bone.

The care of long spiral subtrochanteric fractures and other splitting fractures of the femoral shaft has come under control of Enders pinning techniques if cerclage wires are utilized simultaneously. The prophylactic use of a cerclage wire in the distal femur insures the stability of Enders pinning for routine intertrochanteric fractures.

In the osteoporotic patient, the use of the Enders pins is jeopardized by dissolution of the proximal wall of the femoral fenestration. The basic design of the Enders pin is that of a spring that is distorted upon insertion. While attempting to restore itself, the tension of the spring maintains the integrity of its position. This spring pressure places a severe strain on the proximal edge of the fenestration as insertion takes place and can cause vertical fractures to develop proximally. This weakens the effect of the spring fixation and leads to loosening of the Enders pin and the fixation in the hip thereafter. This phenomena is largely responsible for the less than overwhelming reception that the Enders pinning procedures have received, and this excellent procedure deserves a much greater popularity.

To prevent this type of loosening of the Enders pins, it has been recommended that a cerclage wire be placed around the distal femur just above the fenestration in order to reinforce this area. Usually this is done prophylactically on every case in which osteoporosis is a factor. With this support in place, it is rarely necessary to stack more than three pins, no matter how wide the medullary cavity.

The effectiveness of the cerclage wire has proven itself, but the cerclage procedure itself has proved difficult and exasperating in many cases. The need for an instrument to pass wire around the femoral shaft without excessive exposure or stripping of musculature is most evident when existing wire passer designs are used. The heretofore instruments fail to provide an adequate technique and lengthen the overall procedure appreciably. For the most part the heretofore proposed instruments include C-shaped curves with associated handle structure. Some of these curves are hollow for guiding the orthopedic wire therethrough after the instrument is positioned around the bone. Other instruments include an eyelet opening at the free end of the simple curve through which the wire is threaded during the cerclage procedure.

A new cerclage wire passer is needed which takes into consideration the fact that as the passer is placed around the femoral shaft, it makes contact with the vastus lateralis and the remaining quadriceps musculature on the anterior aspect of the thigh. These muscles effectively block the medial motion of the passer handle so that it becomes difficult to bring the distal end into view in the incision.

BACKGROUND OF THE INVENTION

Accordingly, it is an object of the present invention to provide a cerclage wire passer which is simple in design and easy to use in effectively and efficiently passing orthopedic wire around a bone, such as a femur.

Another object of the invention herein is a cerclage wire passer which overcomes the shortcomings of the prior art by providing a secondary reverse curved segment which accommodates the mass of the quadriceps as the passer moves around and over the femur location where cerclage is desired.

In accordance with the present invention, a cerclage wire passer comprises a proximal portion with handle structure and an S-shaped distal portion with an eyelet hole at the outer end thereof. The S-shaped distal portion includes a primary curved segment and a secondary reverse curved segment positioned between the proximal portion and the primary curved segment.

The primary curved segment and the secondary reverse curved segment are in the same plane. Also, it is preferred that the eyelet hole at the outer end of the S-shaped distal portion is arranged substantially normal to the plane of the primary curved segment and the secondary reverse curved segment. Preferably the handle structure defines a plane arranged substantially normal to the plane of the primary curved segment and the secondary reverse curved segment.

In one of the preferred embodiments of the present invention, the primary curved segment has a radius of approximately $\frac{7}{8}$ inch and the secondary reverse curved segment has a radius of approximately $1\frac{5}{8}$ inch. In another preferred embodiment the primary curved segment has a radius of approximately $1\frac{1}{8}$ inch and the secondary reverse curved segment has a radius of approximately $1\frac{5}{8}$ inch.

The secondary reverse curved segment of the S-shaped distal portion is preferably connected to the proximal portion at an angle in the range of 90° to 180°. In one embodiment of the present invention the secondary reverse curved segment of the S-shaped distal portion is connected to the proximal portion at an angle of about 180° to thereby initially form a straight line extension of the proximal portion. In another embodiment of the present invention the secondary reverse curved segment of the S-shaped distal portion is connected to the proximal portion at an angle of about 125°.

Preferably, the primary curved segment has an outer tip end that includes a flattened area and a blunt point. The eyelet hole is directly behind the flattened area.

The invention herein also involves a method of using the above cerclage wire passer.

BRIEF DESCRIPTION OF THE DRAWING

Novel features and advantages of the present invention in addition to those mentioned above will become apparent to those skilled in the art from a reading of the following detailed description in conjunction with the accompanying drawing wherein similar reference characters refer to similar parts and in which:

FIG. 1 is a top plan view of a cerclage wire passer, according to the present invention;

FIG. 2 is a side elevational view of the cerclage wire passer shown in FIG. 1;

FIG. 3 is a top plan view of another cerclage wire passer, according to the present invention;

FIG. 4 is an end elevational view of the cerclage wire passer shown in FIG. 3;

DETAILED DESCRIPTION OF THE INVENTION

Figure 5:
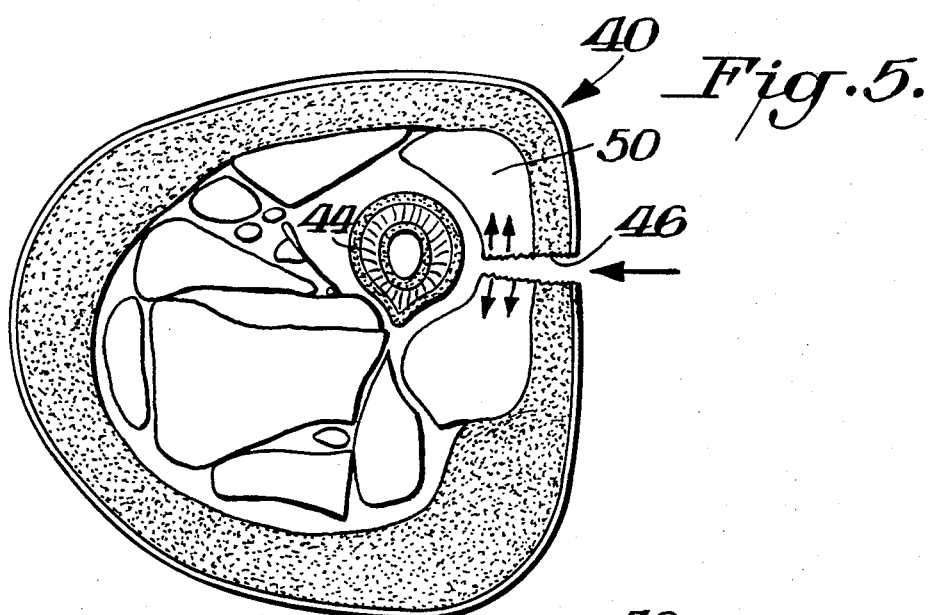
FIG. 5 is a schematic sectional view through a leg illustrating the formation of a small track leading to the femur location where cerclage is desired and the first of several figures illustrating the sequence of using the cerclage wire passer herein.

Referring in more particularity to the drawing, FIG. 1 illustrates a cerclage wire passer 10 comprising a proximal portion 12 and S-shaped distal portion 14 with an eyelet hole 16 at the outer tip end thereof. Handle structure 18 is associated with proximal portion 12. Preferably, wire passer 10 is fabricated from stainless steel rod material having a diameter somewhere in the range of 3/16 inch.

As shown in FIG. 1, the S-shaped distal portion 14 includes a primary curved segment 20 and a secondary reverse curved segment 22 positioned between proximal portion 12 and the primary curved segment. Both the primary and secondary segments lie in the same plane, and it is preferred that the eyelet hole 16 at the outer end of the S-shaped distal portion 20 be arranged substantially normal to the plane of the primary and secondary curved segments.

As is clear from FIGS. 1 and 2, handle structure 18 defines a plane arranged substantially normal to the plane of the primary and secondary curved segments. This arrangement enables sufficient force to be applied to wire passer 10 when manipulating the instrument around a bone during the cerclage procedure. This feature of the invention is explained more fully below.

The primary curved segment 20 of wire passer 10 incudes a flattened area 24 at the outer tip end thereof, the flattened area terminating at a blunt point 26. Eyelet hole 16 is located directly behind flattened area 24.

The geometry of cerclage wire passer 10 is such that the primary curved segment 20 has a radius of approximately ⅞ inch and the secondary reverse curved segment 22 has a radius of approximately 1⅜ inch. Moreover, the secondary reverse curved segment 22 is connected to proximal portion 12 at an angle in the range of 90° to 180°, specifically at an angle of 125°.

FIGS. 3 and 4 illustrate another embodiment of the cerclage wire passer of the present invention and similar parts are identified by similar reference characters. One major difference is that cerclage wire passer 30 of FIGS. 3 and 4 has an S-shaped distal portion 14 which is connected to the proximal portion 12 at an angle of about 180° whereby the secondary reverse curved segment 22 initially forms a straight line extension of the proximal portion. Other geometrical differences include a radius of 1⅛ inch for the primary curved segment 20 of wire passer 30. The radius of curvature of the secondary reverse curved segment 22 of wire passer 30 remains the same, namely 1⅜ inch.

FIGS. 5-9 illustrate the sequence of operation in utilizing the cerclage wire passer of the present invention. While wire passer 10 is specifically illustrated, the procedure is equally applicable to wire passer 30. For illustrious purposes, a leg 40 is shown in section and orthopedic wire 42 is threaded around femur shaft 44 utilizing the cerclage wire passer 10.

Initially, the femur shaft 44 is exposed in the area where the cerclage is desired by the usual muscle splitting or muscle retraction technique. A small track 46 is opened above the anterior surface of the femur and also at the linear aspera posteriorly by dissection with a small periosteal elevator (not shown). The curved periosteal dissector need only be of a small size and move enough tissue to assure that the vascular structures will be separated from the femur when the wire passer is inserted.

Figure 6:
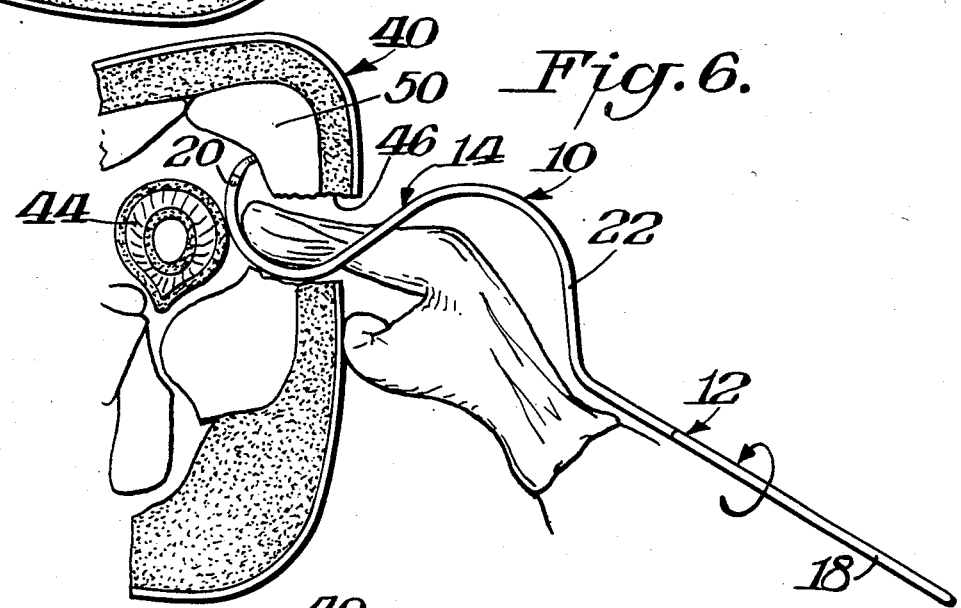
FIG. 6 is a view similar to FIG. 5 illustrating the cerclage wire passer in a horizontal position with the tip end thereof away from the femur and being advanced over the crown of the femur.
Figure 7:
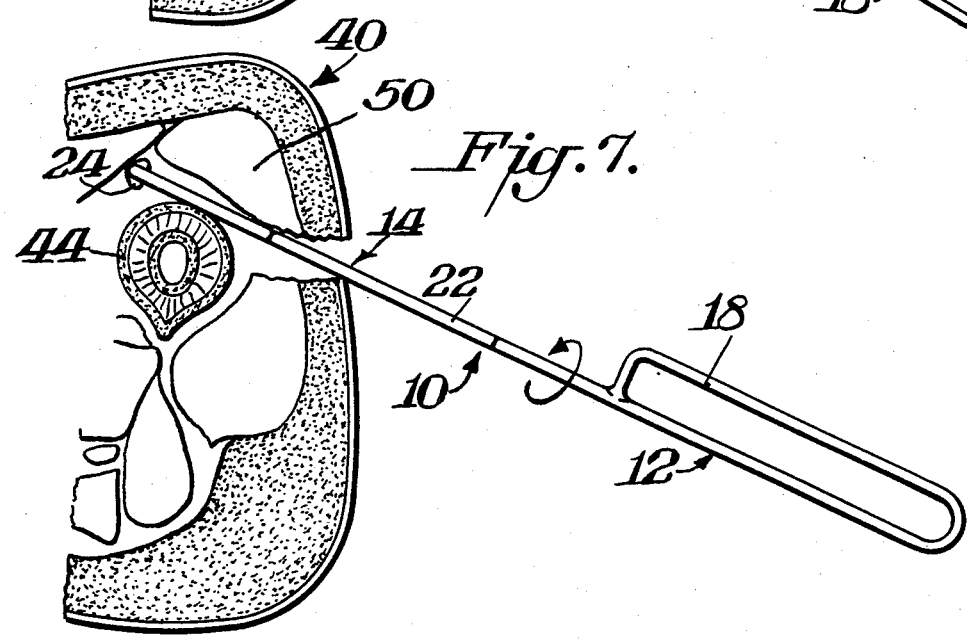
FIG. 7 illustrates the next step in the sequence wherein the cerclage wire passer has been rotated 90° into a vertical position and the tip end is over the crown of the femur.

At the start of the procedure, wire passer 10 is placed in a horizontal orientation with its blunt tip end 26 at the anterior aspect of femur 44. This is illustrated in FIG. 6. In this horizontal mode, the tip end of the wire passer is advanced over the top of femur 44 at which time the instrument is rotated into a vertical orientation, such as shown in FIG. 7. The tip end can then be rotated in a downward direction medially and posteriorly and return into the lateral incision area. This position is shown in FIG. 8.

Next, handle structure 18 is moved gradually upwards thereby forcing the tip end 26 down the medial side of the femur shaft. Applying gradual upwards pressure until the tip 26 appears below femur shaft 44, brings the handle structure 18 across the anterior thigh. As noted above, the orientation of handle structure 18 is such that a flat plane is presented against which the palm of the hand is easily positioned. Upward force at this point in the procedure is applied through the interaction of the plane of handle structure 18 and the palm of the operator.

Figure 8:
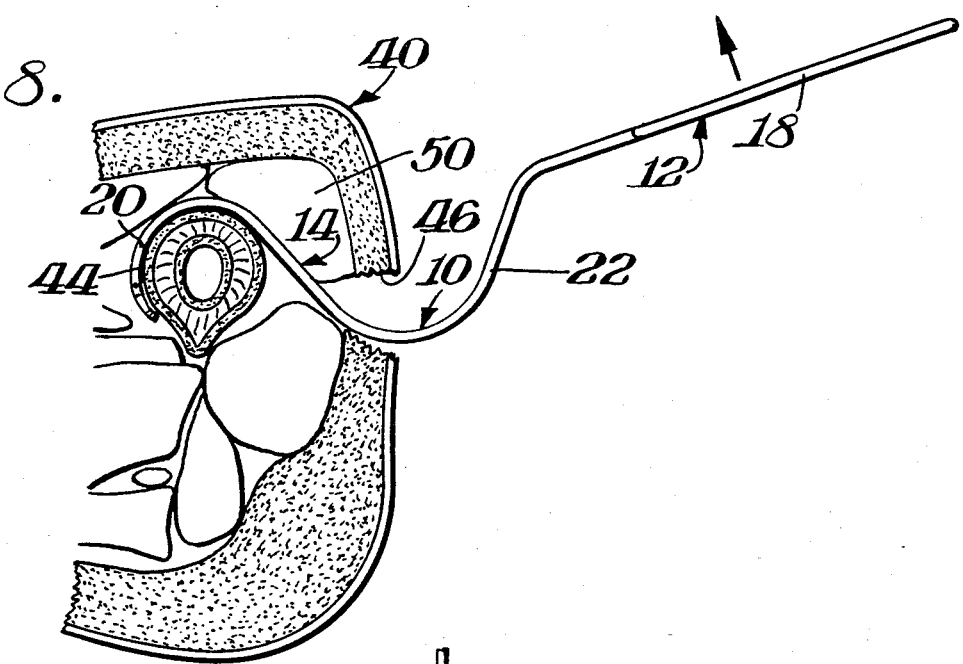
FIG. 8 illustrates the next step in the sequence wherein continued rotation of the cerclage wire passer to a horizontal position forces the tip end down along the medial side of the femur.
Figure 9:
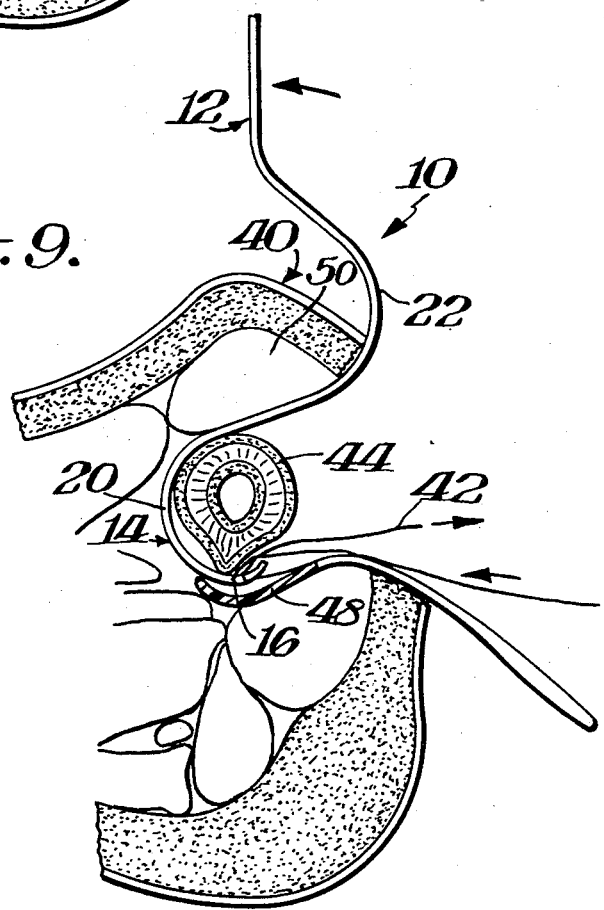
FIG. 9 illustrates the cerclage wire passer rotated in the anterior direction until the tip end appears below the femur.

The last mentioned step moves the wire passer 10 from the position of FIG. 8 to the one of FIG. 9. The tip of the wire passer is then easily exposed by slipping a spoon 48 beneath the flattened area 24 and eyelet hole 16. Orthopedic wire 42 to be passed is then threaded through the eyelet hole by making a small hook in the wire at the end thereof and catching it through the fenestration. The procedure is then reversed and the handle structure 18 is pulled back upwards over the thigh and back down. Wire passer 10 is then placed in its lateral or horizontal position and slipped out of the opening 46. Hence, wire 42 is brought completely around femur shaft 44. The wire is then tightened to draw in fracture fragments or to provide the prophylactic bolster noted above. This is accomplished with a wire tightener (not shown) designed to complete the procedure by tightening, twisting, and breaking off the orthopedic wire.

As is clear from FIGS. 5-9, the primary curved segment 20 of either wire passer 10 or 30 is dimensioned in accordance with the general size of the bone around which segment 20 is passed. On the other hand, the function of secondary reverse curved segment 22 of either wire passer 10 or 30 is to neutralize the tissue and muscular mass adjacent the bone being cerclaged and eliminate that mass as a block. In the above example the quadriceps mass 50 was neutralized by the secondary reverse curved segment 22 and eliminated as a block which otherwise would have prevented the distal tip end 26 of wire passer 10, 30 from reaching the surgical field of view.

What is claimed:

1. A cerclage wire passer for encircling a femur bone with orthopedic wire comprising a proximal portion with handle means and an S-shaped distal portion with an eyelet hole at the outer end thereof, the S-shaped distal portion including a primary curved segment constructed and arranged to fit around the femur bone being cerclaged and a secondary reverse curved segment positioned between the proximal portion and the primary curved segment constructed and arranged to accommodate the quadriceps mass surrounding the bone.

2. A cerclage wire passer as in claim 1 wherein the primary curved segment and the secondary reverse curved segment are in the same plane.

3. A cerclage wire passer as in claim 2 wherein the eyelet hole at the outer end of the S-shaped distal portion is arranged substantially normal to the plane of the primary curved segment and the secondary reverse curved segment.

4. A cerclage wire passer as in claim 2 wherein the handle means defines a plane arranged substantially normal to the plane of the primary curved segment and the secondary reverse curved segment.

5. A cerclage wire passer as in claim 1 wherein the primary curved segment has a radius of approximately $\frac{7}{8}$ inch and the secondary reverse curved segment has a radius of approximately $1\frac{5}{8}$ inch.

6. A cerclage wire passer as in claim 1 wherein the primary curved segment has a radius of approximately $1\frac{1}{8}$ inch and the secondary reverse curved segment has a radius of approximately $1\frac{5}{8}$ inch.

7. A cerclage wire passer as in claim 1 wherein the secondary reverse curved segment of the S-shaped distal portion is connected to the proximal portion at an angle in the range of 90° to 180°.

8. A cerclage wire passer as in claim 7 wherein the secondary reverse curved segment of the S-shaped distal portion is connected to the proximal portion at an angle of about 180° whereby the secondary reverse curved segment initially forms a straight line extension of the proximal portion.

9. A cerclage wire passer as in claim 7 wherein the secondary reverse curved segment of the S-shaped distal portion is connected to the proximal portion at an angle of about 125°.

10. A cerclage wire passer as in claim 1 wherein the primary curved segment has an outer tip end including a flattened area and a blunt point.

11. A cerclage wire passer as in claim 10 wherein the eyelet hole is directly behind the flattened area.

12. A cerclage wire passer as in claim 11 wherein the primary curved segment and the secondary reverse curved segment are in the same plane, and the eyelet hole is arranged substantially normal to the plane of the primary and secondary segments.

* * * * *